(12) United States Patent
Grune (10) Patent No.: US 8,858,922 B2
(45) Date of Patent: Oct. 14, 2014

(54) BROAD SPECTRUM UVA STABLE, NON-TOXIC, ZINC OXIDE BASED COMPLEX

(75) Inventor: Guerry L. Grune, Virginia Beach, VA (US)

(73) Assignee: 3rd Rock Sunblock, Inc., Virginia Beach, VA (US)

( * ) Notice: Subject to any disclaimer, the term of this patent is extended or adjusted under 35 U.S.C. 154(b) by 0 days.

(21) Appl. No.: 13/503,335

(22) PCT Filed: Nov. 22, 2010

(86) PCT No.: PCT/US2010/057615
§ 371 (c)(1),
(2), (4) Date: Jun. 12, 2012

(87) PCT Pub. No.: WO2011/063329
PCT Pub. Date: May 26, 2011

(65) Prior Publication Data
US 2012/0263661 A1   Oct. 18, 2012

Related U.S. Application Data

(60) Provisional application No. 61/281,694, filed on Nov. 20, 2009, provisional application No. 61/281,695, filed on Nov. 20, 2009.

(51) Int. Cl.
*A61K 8/00* (2006.01)
*A61Q 17/04* (2006.01)
*A61K 8/02* (2006.01)
*A61K 33/30* (2006.01)
*A61K 33/02* (2006.01)
*A61K 31/315* (2006.01)
*A61K 8/27* (2006.01)
*A61K 8/04* (2006.01)

(52) U.S. Cl.
CPC . *A61K 8/27* (2013.01); *A61Q 17/04* (2013.01); *A61K 8/044* (2013.01); *A61K 2800/58* (2013.01)
USPC ............. 424/59; 424/401; 424/641; 424/719; 252/588; 252/589; 514/494

(58) Field of Classification Search
None
See application file for complete search history.

(56) References Cited

U.S. PATENT DOCUMENTS

| | | | | |
|---|---|---|---|---|
| 5,209,860 | A * | 5/1993 | Trivett | 508/170 |
| 5,340,567 | A * | 8/1994 | Cole et al. | 424/59 |
| 5,573,753 | A * | 11/1996 | Tapley | 424/59 |
| 5,914,101 | A * | 6/1999 | Tapley et al. | 424/59 |
| 6,368,579 | B1 * | 4/2002 | Barr | 424/59 |
| 6,464,965 | B1 | 10/2002 | Chiarelli et al. | |
| 6,500,411 | B2 | 12/2002 | Sengupta et al. | |
| 6,540,986 | B2 | 4/2003 | Lukenbach et al. | |
| 6,866,841 | B2 | 3/2005 | Grune | |
| 7,014,842 | B2 | 3/2006 | Dueva-Koganov et al. | |
| 8,309,063 | B2 | 11/2012 | Sengupta et al. | |
| 2005/0013781 | A1 | 1/2005 | Dueva-Koganov et al. | |
| 2006/0280702 | A1 | 12/2006 | Sengupta et al. | |
| 2007/0286826 | A1 * | 12/2007 | Grune | 424/59 |
| 2007/0286856 | A1 * | 12/2007 | Brown et al. | 424/133.1 |
| 2008/0219939 | A1 * | 9/2008 | Grune | 424/59 |
| 2008/0233060 | A1 * | 9/2008 | Grune | 424/59 |

OTHER PUBLICATIONS

Gordon et al.; "Estrogenic Potency of Many Popular Sunscreens and Its "Non-Active" Components Detected Using the Lumi-Cell ER Bioassay"; ISPAC—General, Dioxin (2005), #1145, pp. 2685-2689.*
"The Immune System", an online disclosure provided by New Millennium Enterprises; dated Nov. 14, 2008, downloaded Jul. 11, 2013.*
Fallene, Ltd.; Total Block (RTM) Clear SPF 65; Fallene. com; reference copyrighted 2006, downloaded Jun. 21, 2013.*
Kampolo, Kelly P.; South Beach Sun Quality Sun Care; Brazen Dark Tanning Carrot Oil; Dated via Internet Wayback to Nov. 28, 2006; downloaded Jul. 13, 2013.*
Essential Care™; downloaded Jul. 13, 2013; state of the prior art definition for cetearyl glucoside.*
Essential Care™; downloaded Jul. 13, 2013; state of the prior art definition for coco glucoside.*
Skinfopedia; http://skinfopedia.com/Cetearyl Polyglucose; downloaded Jun. 21, 2013 as a state of the prior art showing for an alternate definition of cetearyl glucoside.*
http://www.epatentmanager.com/3rdrock/superior.html#http://www.epatentmanager.com, 3rd Rock Sunblock, Inc. website, copyrighted 2006, downloaded Jan. 7, 2014.

(Continued)

*Primary Examiner* — Jeffrey T Palenik
(74) *Attorney, Agent, or Firm* — ePatentManager.com; Guerry L. Grune (57) ABSTRACT

Disclosed is a new composition of matter that is a compound which also is presented as a dispersion with broad UVA and UVB spectral absorption stability, heat absorption, and insulation properties, anti-microbial, water resistance, and high SPF properties. The composition of matter is a zinc oxide complex that is provided with distilled water buffered to a pH of greater than 10 using ammonium hydroxide, L-arginine, or other buffering agents, and zinc oxide particles. The zinc oxide complex may be dried and rinsed to increase stability. An emollient, such as glycerine, and/or an emulsifier such as a combination of cetearyl alcohol and cetearyl glucoside and/or sodium stearoyl glutamate and/or cetearyl glucoside may also be added to the zinc oxide complex. The zinc oxide complex is made from natural-based, earth-derived, Ecocert® certified ingredients is non-toxic, and may be used or combined with any compound in which UVA/UVB stability is desired. The applications for the zinc oxide complex are numerous and include; roofing materials, composite building materials, automobile and aircraft parts, textiles, wire and cable insulation, use in conductor and semi-conductor technologies, as well as for sunscreens and cosmetics.

34 Claims, 5 Drawing Sheets

(56) References Cited

OTHER PUBLICATIONS http://info.3rdrocksunblock.com/spf8moi.html, 3rd Rock Sunblock, Inc. website, INCI, copyrighted 2010, downloaded Jan. 7, 2014.
http://3rdrock.myshopify.com/colelctions/frontpage/products/3rdrock-spf-30-sunblock, 3rd Rock Sunblock, Inc. website, copyrighted 2014, downloaded Jan. 7, 2014.
MSDS, 3rd Rock Zinc Block(TM), Issued Jan. 8, 2010, Revised Jan. 8, 2010, McCullough.
http://info.3rdrocksunblock.com, 3rd Rock Sunblock, Inc. website, Homepage, copyrighted 2010, downloaded Jan. 7, 2014.
http://info.3rdrocksunblock.com/science.html, 3rd Rock Sunblock, Inc. website, copyrighted 2010, downloaded Jan. 7, 2014.
McCullough & Associates, Proposal email dated Jan. 10, 2010 to G. Grune.

* cited by examiner

BROAD SPECTRUM UVA STABLE, NON-TOXIC, ZINC OXIDE BASED COMPLEX

PRIORITY STATEMENT

This application takes priority under 35 USC 119 from the following provisional applications; Provisional Application No. 61/281,695 entitled "Natural-based, Non-endocrine Disrupting Non-Toxic, SPF Formulation filed Nov. 20, 2009 and Provisional Application No. 61/281,694 entitled "Broad Spectrum UVA Stable, Non-Toxic, Zinc Oxide Based Complex" also filed on Nov. 20, 2009 and under 35 USC 365 (c) of the PCT application number PCT/US2010/057615 filed on Nov. 22, 2012 entitled "Broad Spectrum UVA Stable, Non-Toxic, Zinc Oxide Based Complex". The entire contents of both provisional applications (61/281,694 and 61/218,695) the above referenced applications are also herewith incorporated by reference in the present application.

FIELD OF DISCLOSURE

The present invention generally relates to a unique micronized zinc oxide based complex. The zinc oxide based complex may be incorporated into a number of other compositions to convey outstanding properties including unparalleled UVA and UVB spectral absorption stability and protection from the damaging effects of UV exposure. Such properties derived from natural-based, non-toxic substances are highly desirable for incorporation with products such as thermoplastics, wood preservatives, composite building materials, wire and cable insulation, roofing materials, conductors, semi-conductors, and other insulators. In addition, the present invention also relates to the development of micronized zinc oxide based dispersions capable of sun protection factor (SPF) values up to at least 460 nm with unsurpassed UVA stability in the wavelength range of about 320 nm to about 375 nm. The formulations utilizing these dispersions contain only ingredients derived directly from natural-based, earth-grown substances, and offer enhanced protection when used in sunscreen and sunblock formulations. These formulations are acceptable either as SPF boosting additives in UV sunscreen products or as having an increased ability to protect the user from the complete UV radiation spectrum.

BACKGROUND OF DISCLOSURE

A substance with high UVA and UVB spectral absorption stability, high heat absorption, and insulation capabilities is desired for a number of applications, including wire and cable insulation, wood preservatives, paints, roofing materials, composite building materials, thermoplastics, motor vehicle and aircraft parts, textiles, rubber, and sunscreens, among numerous other uses. With greater public awareness regarding issues of health and the environment, a complex, non-toxic to humans and mammals, derived from natural-based, earth-derived ingredients is preferred in these applications over that of a substance that is potentially harmful to human and/or environmental health. Other ZnO complexes (dispersions) utilize either synthetic or toxic (or both) additives/coatings in order to stabilize the complex. The present application and associated invention describes a ZnO complex which utilizes neither toxicity or are synthetic (such as silicones).

It is instructive to consider the potential damage that UVA and UVB radiation poses to car dashboards and parts of aircraft. The sun's damaging rays are apt to cause these areas on vehicles to crack, crumble, or become otherwise damaged over time, thereby impeding their efficacy and reducing their aesthetic appeal.

Also, wires and cables for outdoor use require some form of insulation or outer coating to prevent their degradation as a result of the heat and ultraviolet radiation produced by the sun. Today, polymers and rubber are primarily used for insulation; however, these insulating products are subject to cracking and may not offer sufficient heat, moisture, electrical or thermal insulating properties as well as UVA/UVB protection.

Using a product that provides high UVA/UVB protection for textile applications such as clothing, window shades, woven and non-woven fabrics could be manufactured with metal oxide materials that include heat and ultraviolet ray absorption properties as well as improved sun protection factors that could help keep wearers free from sunburn and allow for users to obtain products that remain stable in the outdoors for longer time durations.

The present application and associated invention also can be applied to wood preservatives, composite building materials, roofing materials, and even in mirrored glass to protect these products from the harmful effects of UVA and UVB radiation, thus prolonging their efficaciousness in an unobtrusive, relatively inexpensive manner.

Carbon black is a well-known product with similar properties to the disclosed composition of matter: UVA/UVB stability, pigmentation, and heat absorption, are all useful properties. Carbon black is commonly used in rubbers and tires as a filler and reinforcer, in plastics, and in high performance coatings. However, because carbon black is commonly provided as a dust or powder, it poses some health risks, including possible respiratory and eye irritation upon exposure. It is also classified by the International Agency for Research on Cancer as a group 2B carcinogen, indicating that it is possibly carcinogenic to humans. Furthermore, carbon black is not non-endocrine disrupting or non-toxic and can pose some risk to the environment if not disposed of properly. Also, carbon black is limited in its uses because it cannot be applied in products such as sunscreens and cosmetics to protect humans from the sun's dangers. It also does not possess the anti-microbial properties of the present composition provided in this disclosure.

The present disclosure provides a zinc oxide based complex comprising natural-based, earth-derived ingredients exhibiting unparalleled UVA and UVB spectral absorption stability, high SPF values as measured in-vitro, as well as anti-microbial, insulative, and heat absorption properties. Because the complex is derived from natural-based, earth-derived ingredients and substances non-toxic to humans and mammals, it is highly desirable for use in a number of applications where other compounds cannot or should not be used as they may endanger the environment and/or human health.

The present disclosure also provides for a new zinc-oxide based composition of matter in which distilled water is adjusted to a pH of 10 or greater using a buffering agent such as ammonium hydroxide, L-arginine, or sodium hydroxide. Micronized zinc oxide particles are then added to the buffered water while ensuring that the pH remains above 10. The dispersion of the zinc oxide through the buffered water then occurs as the zinc oxide particles disperse in a continuous phase. Normally within 24 hours, a zinc oxide complex is formed which can create a pinhole free thin film layer with high SPF values, ranging from at least 100 nm up to 460 nm when measured in-vitro using the Labsphere UV 2000S Ultraviolet Transmittance Analyzer, available from Labsphere of North Sutton, N.H. and exhibits unparalleled UVA and UVB spectral absorption stability.

In one embodiment an ammonium hydroxide ($NH_4OH$) buffer solution is added to distilled water to attain a pH of preferably between 10.0 and 11.0 before adding the zinc oxide particles to pH adjusted distilled water to avoid zinc hydroxide formation. Hydroxide formation is minimized by continuously adding zinc oxide and not allowing the pH to drop below 10.0. Adding more ammonium hydroxide buffer solution to raise the pH, if the extra addition of zinc oxide reduces the pH, is critical to assure no further reduction of the pH. Within 24 hours the zinc oxide solution pH increases from about 10.0 to about 10.4.

In another embodiment any amine, preferably the amino acid L-arginine, is used in lieu of ammonium hydroxide as a pH buffering agent.

In another embodiment, during the reaction of the zinc oxide in the buffered water, the zinc oxide complex undergoes an endothermic reaction and benefits from chilling at a temperature less than 20 degrees centigrade for a period of between about one hour and about 36 hours, preferably greater than 24 hours.

In another embodiment the zinc oxide complex is dried and rinsed with an aqueous solution buffered with, for example, sodium bicarbonate after the 24 hour cooling period to ensure that all excess ammonia is removed, thus ensuring that the zinc oxide complex is highly stable.

In another embodiment the zinc oxide complex physically comprises a creamy white paste, a semi-solid white cake-like consistency or a solid white powder or block throughout the different stages of drying.

In another embodiment an emollient, preferably glycerine is added to the dried zinc oxide complex to improve the physiochemical stability of the product.

In another embodiment an emulsifier such as cetearyl alcohol, cetearyl glucoside such as TEGO® Care CG 90 supplied by Evonik Industries AG, sodium stearoyl glutamate such as Eumulgin® SG supplied by Cognis Corporations, or a combination of cetearyl alcohol and cetearyl glucoside such as Emuglade® PL 68/50 supplied by Cognis Corporation or a combination of Emuglade® PL 68/50 and Eumulgin® SG is added to the zinc oxide complex to form a fully dispersed zinc oxide complex with unsurpassed UVA spectral absorption stability which also exhibits high SPF values.

In another embodiment the emulsifier used in the zinc oxide complex is at least one glucoside emulsifier selected from the group consisting of cocoyl glucoside, cocoyl glucoside/cetearyl alcohol, cocoyl ethyl glucoside, disodium coco-glucoside citrate, lauryl glucoside, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any mixtures thereof.

In another embodiment the emulsifier used in the zinc oxide complex may include at least one or more additional emulsifiers selected from the group consisting of: butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate and additional emulsifiers selected from the group consisting of: butylated PVP, cetyl alcohol, sodium acrylate/sodium acryloyldimethyltaurate copolymer, diethylhexyl napthalate, and any mixtures thereof.

In another embodiment the zinc oxide complex may include the addition of sodium stearoyl glutamate, such as Eumulgin® SG, sodium N-stearoyl L-glutamate, dioctyldodecyl stearoyl glutamate, TEA-cocoyl glutamate, TEA-lauryl glutamate, TEA-stearoyl glutamate, aluminum stearoyl glutamate, monosodium glutamate, disodium glutamate and any mixtures thereof.

In another embodiment adding an emollient or emulsifier to the zinc oxide complex improves the UV spectral absorption stability.

In another embodiment the emulsifier used is heated to a temperature between about 60 and about 100 degrees centigrade before being added to the zinc oxide complex.

In another embodiment the zinc oxide complex is heated to a temperature of between about 60 and about 100 degrees centigrade to allow for the addition of the chosen emulsifier without preheating the chosen emulsifier.

In another embodiment the zinc oxide complex reflects or absorbs all UVB radiation from about 290 nanometers (nm) to about 320 nm without any degradation in spectral absorption thus allowing for complete UVB protection.

In another embodiment the zinc oxide complex reflects or absorbs UVA radiation from about 320 nm to about 375 nm without degradation of spectral absorption thus allowing for complete UVA protection.

In another embodiment the zinc oxide based formulation shows a sharp UV spectral absorption band edge at about 375 nm, which corresponds with the spectral optical band gap of zinc oxide.

In another embodiment of the disclosure the zinc oxide complex is incorporated into SPF sunscreen or sunblock products, body care products and cosmetics to provide users with protection from harmful ultraviolet radiation.

In another embodiment of the disclosure includes incorporating the zinc oxide complex into wire and cable insulation to provide the insulation with unparalleled protection from ultraviolet radiation increasing the functional lifetime of the insulation.

In another embodiment of the invention the zinc oxide complex is used in thermoplastics to provide protection across the broad UVA/UVB radiation spectrum and increasing the functional lifetime of the thermoplastic materials and products.

In another embodiment the zinc oxide complex is used in wood and metal coatings to prevent degradation or damage resulting from exposure to ultraviolet radiation.

In another embodiment the zinc oxide complex is applied to materials used in the construction of various aircraft parts and car dashboards to prolong their appearance and prevent a decrease in their functionality as a result of damage from ultraviolet radiation.

In another embodiment the zinc oxide complex is used in woven and non-woven textiles, such as clothing and window drapes, to convey heat absorption and UVA/UVB protective properties, as well as provide high SPF values to prevent injury from the sun's rays.

In another embodiment the zinc oxide complex may be used in rubber products and tires in the same manner as carbon black.

In another embodiment, the zinc oxide complex may be incorporated into roofing materials to increase their resistance to the development of cracks and provide adequate insulation and protection from exposure to UVA and UVB rays for the building.

In another embodiment the anti-microbial properties of the zinc oxide complex can be optimized in applications that require such anti-microbial properties.

In another embodiment the zinc oxide complex is provided as a paste or dried powder and functions as a UV stabilizing component for most organic or inorganic compounds.

In another embodiment the zinc oxide complex is provided in paste form and may be used in lieu of UVA/UVB stabilizing compounds or as an alternative to carbon black.

In another embodiment adding carrot oil to zinc oxide complex acts allows for the carrot oil to act as an emulsifier as the carrot oil contains a high concentration of natural glucosides stabilizing the complex.

In another embodiment adding carrot oil to the zinc oxide complex acts as a natural colorant imparting a darker, UV absorbing color to the final product formulations.

In another embodiment the zinc oxide dispersion performs as an exceptional water-resistant barrier and is perspiration resistant. The dispersion has water-resistant properties similar in performance, to Antaron Ganex®, a copolymer of vinylpyrrolidone and long chain alpha-olefins, manufactured by International Specialty Products Inc., however, the ZnO dispersion of the present disclosure is in addition, UV stable, non-toxic to humans and non-endocrine disrupting (the Ganex exhibits none of these attributes).

In another embodiment the zinc oxide complex is added to interior and exterior composite building materials to increase resistance to degradation, discoloration, deformation, and to physical and mechanical stresses due to UV exposure.

In another embodiment the degree of the water-resistant properties can be adjusted by use of different emulsifiers when mixing the zinc oxide dispersion. Emulsifiers include, but are not limited to cetearyl alcohol, sodium stearoyl glutamate such as Eumulgin® SG, cetearyl glucoside such as TEGO® Care CG 90 or a combination of cetearyl alcohol and cetearyl glucoside such as Emuglade® PL 68/50 or a combination of Emuglade® PL 68/50 and Eumulgin® SG. The use of Phospolipon® 90G supplied by American Lechithin Company in Oxford, Conn. and other phospholipids and phosphotidyl cholines may also be useful emulsifiers.

In another embodiment the mixing and blending characteristics of the zinc oxide complex into other materials can be controlled or adjusted by the use of different emulsifiers during the mixing process. The emulsifier can be chemically matched to the chemical system to which it is added. Emulsifiers include, but are not limited to cetearyl alcohol, cetearyl glucoside, sodium stearoyl glutamate such as Eumulgin® SG, cetearyl glucoside such as TEGO® Care CG 90 or a combination of cetearyl alcohol and cetearyl glucoside such as Emuglade® PL 68/50 or a combination of Emuglade® PL 68/50 and Eumulgin® SG.

It is well documented that human skin, and most mammalian skin, is sensitive to sunlight and artificial light containing radiation of wavelengths between about 290 nanometers (nm) and about 400 nm. Ultraviolet radiation of wavelengths between about 290 nm and 320 nm (UVB region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UVA region) and the adverse effects of such radiation on human skin. The radiation between 320 nm and 400 nm also contributes to the premature aging of the skin and also has been implicated in causing DNA mutation. In addition, recent studies indicate that chronic sun exposure limits the immune capabilities of the skin. There is some evidence that a tan will offer some protection against burning, but that the tan is quite ineffectual against many other types of solar damage, and there is no evidence that a tan increases the immune function of human skin Protection against UVC radiation is generally not a major concern, i.e., in contrast to the dangers posed by UVA and UVB radiation.

A study by Margaret Schlumpf from the Institute of Pharmacology and Toxicology at the University of Zurich supports earlier health concerns regarding the use of endocrine disrupting organic substances in nearly all UV screening chemicals used in sunscreens.

Chemical sunscreens contain from about 3% to about 26% of one or more UV-absorbing chemicals. When applied to the surface of the skin as a thin film, for example, about 10 um to about 15 um thickness, these chemicals act as a filter to diminish the penetration of UV radiation to the cells of the epidermis. These sunscreens are typically applied as a cream, oil, lotion, alcohol, spray or gel vehicle and they are usually colorless because they do not contain any visible light-absorbing chemicals. The most widely used chemical sunscreens contain, for example, para-aminobenzoic acid (PABA), PABA esters (glyceryl PABA, amyldimethyl PABA and octyldimethyl PABA), benzophenones (oxybenzone and sulisobenzone), cinnamates (octylmethoxy cinnamate and cinoxate), salicylates (homomethyl salicylate) and anthranilates.

It is desirable to provide a UV protective product that has the following attributes: protection in the UVA and UVB long range and short range ultraviolet radiation ranges; maintenance of coverage, such as, waterproof or at least water-resistant and perspiration proof; application and use convenience, such as, ease of application, invisibility or at least semi-transparency, non-staining and non-greasy; cytoprotective, anti-oxidative and immuno-enhancing properties; and freedom from irritation as a result of its ingredients, in particular, its active sun-block or sunscreen ingredients should also be void of any known or suspected endocrine disrupters.

Physical sunscreens, a compound typically suspended in a cream or lotion, on the other hand, comprise UV-absorbing particles that are relatively physiologically inert. Materials frequently utilized for this purpose include kaolin, talc and two metal oxides; titanium dioxide and zinc oxide, as well as silica and some hydroxides of metals such as aluminum hydroxide. The titanium and zinc oxides are not associated with inflammatory skin reactions.

The physical sunscreen products are, however, typically messy and occlusive. Moreover, they form a visible, opaque, colored (such as white) layer on the surface of the skin, which is cosmetically unacceptable to many who are in need of sunscreen protection. This causes many such individuals to forego the use of these products. The color of these compositions is attributable to the optical properties of the particles from which these materials are formed. These properties are at least partially dependent upon the size of these micronized particles, which typically have a fairly "standard" range of diameters, measured in tenths of a micron, for example, about 0.1 µm to about 0.9 µm.

One current measure of effectiveness of a sun protective product is indicated by its sun protection factor (SPF). The sun protection factor is the ratio of the amount of exposure or dose required to produce minimal erythema in protected skin to the amount of exposure required to produce the same reaction in unprotected skin. The absolute dose differs for each human and for each mammal, and is largely dependent on genetic predisposition and ethnic origin of the human. If a human or other mammal would normally require ten minute exposure to sunlight to develop a minimal erythema reaction, then using an SPF 15 sunblock should allow for tolerance of up to 150 minutes of sunlight before developing a minimal erythema. Relatively recent public awareness of the problems of exposure to sunlight has led to a demand for sunblock products with high SPF values, i.e., at or above SPF 8.

Greater public awareness of the harmful effects of exposure to excessive solar radiation has therefore resulted in an increased use of sunscreen products by the public, coupled with a call for improved sunscreen materials free of the drawbacks described above by those whose livelihood and/or leisure activities cause them to be exposed to any solar radiation. The newly proposed FDA requirements will include UVA stability verification. These requirements will supersede the current FDA monograph issued in 1978.

One study, entitled "In vitro assessments of UVA protection by popular sunscreens available in the United States" by Steven Q. Wang, M D, A Joseph W. Stanfield, M S, and Uli Osterwalder, MSc, illustrates the need for a sunscreen with improved UVA protection capabilities. Its objective was to assess in vitro the degree of UVA protection provided by 13 popular sunscreen products that are commercially available in the United States accomplished through assessment of the 13 products according to the FDA Proposed Amendment of Final Monograph (Aug. 27, 2007), the European Commission Recommendation—the Colipa and critical wavelength methods, and the United Kingdom's Boots star rating system. The results showed that based on the new FDA-proposed guidelines, 8 products achieved the medium protection category, and 5 products achieved high protection. The latter 5 products also fulfilled the UVA protection based on the Colipa guideline desired by the European Commission Recommendation. Nine products achieved the desired critical wavelength value of 370 nm or higher. Based on the United Kingdom's Boots star rating system, 6 products achieved a rating of 3 stars, and the remaining 7 products achieved no star rating. The study concluded that the majority of the tested sunscreens offered a medium degree of UVA protection. Compared with the sunscreens in the past, this study shows that UVA protection of sunscreens has improved while still indicating that improved protection is desired.

Other examples of relevant art are described below:

U.S. Pat. No. 5,587,148 to Mitchell, Kim, et al., and assigned to SunSmart, Inc., describes a topical sunblock formulation for shielding skin from ultraviolet radiation comprising a substantially colorless dermatologically acceptable liquid carrier and micronized particles of zinc oxide containing some lead, arsenic, cadmium, and mercury. The particles are uniformly dispersed in the liquid carrier to form the sunblock formulation in an amount sufficient to protect the skin from hazardous effects of UVA and UVB radiation.

U.S. Pat. No. 5,562,897 to Mitchnick, Mark, et al., and assigned to Silitech Inc. and SunSmart, Inc., describes a process for protecting the skin from the sun's ultraviolet rays in which an effective protecting concentration of a hydrophobic titanium dioxide, prepared by the reaction of a silicone compound conforming to a specific structure with titanium dioxide, is applied to the skin.

U.S. Pat. No. 5,536,492 to Mitchnick, Marck, et al., and assigned to Silitech, Inc. and SunSmart, Inc., describes a process for protecting the skin from the sun's ultraviolet rays in which an effective protecting concentration of a hydrophobic zinc oxide, prepared by the reaction of a silicone compound conforming to a specific structure with zinc oxide, is applied to the skin.

U.S. Pat. No. 5,531,985 to Mitchell, Kim, et al., and assigned to SunSmart, Inc., describes a substantially transparent topical sunblock formulation for shielding skin from ultraviolet radiation comprising a plurality of particles of a visibly transparent UV absorbing crystal glass free of fractures and imperfections dispersed within a substantially colorless dermatologically acceptable liquid carrier in an amount effective to shield the skin from the hazardous effects of ultraviolet radiation.

EP 0935959B1 to Gers-Barlag, Heinrich, et al., and assigned to Beiersdorf Aktiengesellschaft, describes the use of beeswax for increasing the UVA protection performance of cosmetic or dermatological preparations comprising at least one customary UVA filter substance and/or one broadband filter substance which also affords protection against UV radiation with a wavelength greater than 335 nm.

World Patent Application WO 2008108756A1 to Guerry Grune, and not assigned, describes a formulation comprising a combination of at least one inorganic sunblocking or sunscreen agent that is non-endocrine disrupting, at least one emollient that is non-endocrine disrupting, and an oil component capable of protecting skin from the harmful effects of radiation, both sunlight and ultraviolet light. The oil is a carrier oil, an essential oil, or both.

U.S. patent application No. 20090185991A1 to Spaulding, Laura A., et al., and assigned to Playtex Products, Inc., describes a photoprotective composition comprising a synergistic triplet combination of zinc oxide, styrene/acrylate copolymer, and glycol. The synergistic triplet combination conveys a higher SPF value to the photoprotective composition compared to a similar composition that does not include the triplet combination.

U.S. Pat. No. 6,544,530 to Friedman, Doron, and assigned to J.P.M.E.D., Ltd., describes a topically applicable stable oil-in-glycerin composition comprising a continuous glycerin phase, at least one vegetable oil, at least one biodegradable emulsifier, and at least one bioactive essential oil component for topical, external use on skin and mucosal surfaces. The bioactivity of this latter component is selected from the group consisting of topical anti-inflammatory activity, topical anti-fungal activity, topical anti-bacterial activity, topical anti-parasitic activity, and topical anti-viral activity. The essential oil is a volatile mixture of esters, aldehydes, alcohols, ketones, and terpenes.

U.S. Pat. No. 5,340,567 to Cole, Curtis A., et al., and assigned to Johnson and Johnson Consumer Products, Inc., describes a sunscreen composition comprising an extending medium and a synergistic combination of titanium dioxide and zinc oxide present in a weight ratio of from about 1:25 to 10:1. The total of the titanium dioxide and zinc oxide is between about 4.0% to about 25.0% by weight of the total composition.

U.S. Pat. No. 5,916,542 to Fossati, Antonio, and not assigned, describes an antisolar screening and antierythema mixture made of natural substances efficient against damaging UV rays. The mixture comprises amino acids, such as tryptophan, histidine, and phenylalanine, vitamins or provitamins, such as vitamins B6, A, and E, tocopherols, and bioflavonoids, nucleoderivatives, such as nucleosides, nucleotides, and uric acid, and vegetable extracts, such as carrots, bilberry, and aloe.

U.S. Pat. No. 5,945,090 to Randall, William B., et al., and assigned to Randall Products International, describes a quick-drying, waterproof, non-slip sunscreen composition with 1% to 41% by weight of at least one UVA and one UVB component, 1% to 6% stryrene acrylates copolymer, 1% to 49% tapioca powder, and 1% to 4% macrocystis spyriferae algae extract and aloe barbadensis Miller.

German Patent Application No. DE3642794A1 to Iwaya, Katsuma, et al., and assigned to Kao Corp., Tokio/Tokyo, JP, describes a cosmetic composition for preventing sunburn which contains 1% to 25% zinc oxide of a particle size of 70 um to 300 um. It further indicates that the composition may also contain titanium dioxide of a particle size of 30 um to 70 microns um. This composition is undesirable due to its whiteness characteristics when applied to the skin concurrent with high SPF levels.

EP 0619999A2 to Dahms, Gerb Herbert, and assigned to Tioxide Specialties Limited, describes a process for preparing sun protection compositions in which an aqueous dispersion of a particulate metallic oxide is mixed with an emulsifier and an oil phase to form an oil-in-water emulsion and also with a hydrophobic organic sunscreen. The amount of metallic oxide present in the emulsion is up to 10% by weight and the amount of hydrophobic organic sunscreen present is up to 7% by weight. This process produces a composition with a higher SPF than would be expected with an additive effect produced by the quantities of metallic oxide and organic sunscreen used.

U.S. patent application No. 20060008427A1 to Dueva, Olga V., et al., and assigned to Playtex Products, Inc., describes a photoprotective composition comprising a synergistic combination of at least one sunscreen agent and at least one carotenoid, The combination results in a higher SPF value for the photoprotective composition than a similar photoprotective composition without the combination.

U.S. patent application No. 20030215522A1 to Johnson, Eric Scott, et al., and assigned to The Procter and Gamble Company, describes a composition comprising an effective amount of a zinc containing material with an aqueous solubility within the composition of less than about 25% by weight at 25 degrees centigrade, between 5% and 50% of a surfactant, and between 40% and 96% water. The pH of the composition is greater than 7.

U.S. patent application No. 20060280702A1 to SenGupta, Ashoke K., et al., and assigned to AMCOL International Corporation, describes a stable, oil-in-water emulsion-based sunscreen composition with at least one water-insoluble, organic UV-absorber with a water-solubility of less than 0.1% by weight, contained in the oil phase of the sunscreen emulsion comprising zinc oxide particles with no prior coating dispersed in the water phase of the sunscreen emulsion, at least one non- or low-foaming, non-cationic, hydrophilic polymer, capable of dispersing or deflocculating the zinc oxide particles but incapable of thickening an aqueous composition to a viscosity of greater than 100 cps at 25 degrees centigrade, at least one phenolic polymer capable of functioning as a dispersing or deflocculating agent for particulate material, and a buffering agent for the water phase of the sunscreen emulsion.

U.S. Pat. No. 6,264,961 to Ansmann, Achim, et al., to Henkel Kommanditgesellschaft auf Aktien, describes an oil-in-water emulsifier composition comprising an alkyl or alkenyl oligoglycosides, a fatty acid N-alkyl polyhydroxyalkylamide, or an acyl glutamate, and a polyol polyhydroxystearate with a ratio by weight of 90:10 to 10:90.

An article entitled "In Vitro and In Vivo Estrogenicity of UV Screens" by Margaret Schlumpf and others published in Environmental Health Perspectives in March, 2001, confirms that many current UV-protection products may pose health concerns in the form of endocrine disruption, especially in relation to endocrine functions in reproduction and development.

The present invention provides for a zinc oxide based aqueous dispersion for high SPF formulations that shield skin from ultraviolet radiation, having an effective amount of distilled water utilizing a basic pH buffering agent such as ammonium hydroxide, L-arginine or sodium hydroxide, and a zinc oxide powder or solid which is dispersed in a base of a polyol or a glucoside, or other Ecocert® certified emulsifiers or emollients. The dispersion is produced from zinc oxide and buffered water by ensuring that the pH of the water remains above 10.0 during the dispersion reaction of the zinc oxide. The fully reacted zinc oxide dispersion creates pinhole free films providing unexpectedly high SPF values due to exceptionally uniform film coverage.

An embodiment of the disclosure is to provide a zinc oxide based dispersion with high SPF values for use in UVA and UVB radiation resistant sunscreen and sun-blocking compositions.

In another embodiment the zinc oxide based SPF complex is composed of natural-based, earth-grown ingredients which at least meet Ecocert® certifications, and are non-toxic, non-endocrine disrupting, cytoprotective, anti-oxidative and immuno-enhancing substances.

In another embodiment the zinc oxide based dispersion contains chemically stable micronized zinc oxide with or without surface treatments.

In another embodiment the zinc oxide based dispersion exhibits an SPF value of up to about 460 as determined by in vitro testing using a Labsphere UV 2000S Ultraviolet Transmittance Analyzer, available from Labsphere of North Sutton, N.H.

In another embodiment during the reaction of the zinc oxide in the buffered water, the dispersion undergoes an endothermic reaction and benefits from chilling the dispersion at a temperature less than about 20 degrees centigrade.

In another embodiment an ammonium hydroxide ($NH_4OH$) buffer solution is added to distilled water to attain a pH of preferably between about 10.0 to about 11.0 before adding zinc oxide to the water to avoid zinc hydroxide formation by continuously adding zinc oxide until the pH is near 10, not allowing the pH to drop below 10 and then adding more ammonium hydroxide buffer solution to raise the pH and adding zinc oxide to reduce the pH until has all the desired zinc oxide has fully reacted, with a desired pH end point of greater than 9.5.

In another embodiment the dispersion of buffered distilled water and zinc oxide must be allowed to react at a temperature of less than 20 degrees centigrade for between about one hour and about 36 hours, preferably greater than 24 hours.

In another embodiment the zinc oxide dispersion physically comprises a creamy white paste, a semi-solid white cake-like consistency or a solid white powder or block during the different stages of drying.

In another embodiment the zinc oxide based dispersion is washed and dried into a semi-solid white cake-like consistency to remove moisture and then rinsed with alkaline distilled water prepared with sodium bicarbonate brought to a pH of about 7.5 to about 8.5 before re-drying for between about one hour and about 36 hours. The zinc oxide based dispersion then is formed with glycerine or other polyols, emulsifiers or emollients additions (a minimum of 1.0 wt. %) and allowed to stay fully dispersed in the glycerine base preferably greater than 24 hours before compounding with other sunscreen formulation components.

In another embodiment an emulsifier such as cetearyl alcohol, cetearyl glucoside, sodium stearoyl glutamate such as EUMULGIN® SG supplied by Cognis Corporation or a combination of cetearyl alcohol and cetearyl glucoside such as EMUGLADE® PL 68/50 supplied by Cognis Corporation or a combination of cetearyl alcohol and cetearyl glucoside such as EMUGLADE® PL 68/50 and sodium stearoyl glutamate such as EUMULGIN® SG is added to the zinc oxide dispersion to form a fully dispersed zinc oxide compound with inherent UV stability and high SPF values.

In another embodiment adding an emollient or emulsifier to the zinc oxide based dispersion improves the UV stability.

In another embodiment adding an emollient or emulsifier with the zinc oxide based dispersion and allowing to react for between about one hour and about 36 hours, preferably greater than 24 hours produces an exothermic reaction.

In another embodiment adding carrot oil to the fully dispersed zinc oxide based compound decreases the pH wherein adding L-arginine increases the pH to a value greater than about 9.

In another embodiment adding carrot oil to the fully dispersed zinc oxide based compound provides a natural colorant emulsifier with a high concentration of natural glucosides as well as an additional SPF boost by imparting a darker, UV absorbing color to the final SPF formulations.

In another embodiment adding carrot oil to the fully reacted dispersed zinc oxide based compound is preferred when the dispersion includes glycerine.

In another embodiment the zinc oxide based SPF formulation reflects or absorbs all UVB radiation from about 290 nm to about 320 nm without degradation in the UV absorption spectra or in UVB protection.

In another embodiment the zinc oxide based SPF formulation reflects or absorbs UVA radiation from about 320 nm to about 375 nm without degradation in the UV absorption spectra or in UVA protection.

In another embodiment the emulsifier in the fully dispersed zinc oxide based compound contains an emulsifier composition of cetearyl alcohol and cetearyl glucoside such as EMUGLADE® PL 68/50.

In another embodiment the emulsifier used to provide zinc oxide based SPF formulations is at least one glucoside emulsifier selected from the group consisting of cocoyl glucoside, cocoyl glucoside/cetearyl alcohol, cocoyl ethyl glucoside, disodium coco-glucoside citrate, lauryl glucoside, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any mixtures thereof.

In another embodiment the emulsifier used to provide zinc oxide based SPF formulations is at least one or more additional emulsifiers selected from the group consisting of: butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate and additional emulsifiers selected from the group consisting of: butylated PVP, cetyl alcohol, sodium acrylate/sodium acryloyldimethyltaurate copolymer, diethylhexyl napthalate, and any mixtures thereof.

In another embodiment the zinc oxide based SPF formulations may include the addition of sodium stearoyl glutamate such as EUMULGIN® SG, sodium N-stearoyl L-glutamate, dioctyldodecyl stearoyl glutamate, TEA-cocoyl glutamate, TEA-lauryl glutamate, TEA-stearoyl glutamate, aluminum stearoyl glutamate, monosodium glutamate, disodium glutamate and any mixtures thereof.

In another embodiment the zinc oxide based SPF formulations may be used in a variety of cosmetic and body care products including lipsticks, eye-shadows, foundations, moisturizers, rouges and the like to prevent damage to underlying skin by the action of solar UV radiation.

In another embodiment the zinc oxide based SPF formulations may be used as a component within sunscreen, cosmetic or body care formulations providing unsurpassed UVA/UVB stability between about 290 nm and about 375 nm.

In another embodiment the zinc oxide based SPF formulations contain many components that are known to impart dermalogical healing properties such as anti-inflammatory or anti-microbial effects when topically applied to skin. These components include, but are not limited to zinc oxide, together with aloe and vitamin E.

In another embodiment the zinc oxide used for SPF formulations performs as an exceptional water-resistant barrier and is perspiration resistant. It has water-resistant properties similar in performance, to Antaron Ganex®, a copolymer of vinylpyrrolidone and long chain alpha-olefins, manufactured by International Specialty Products Inc., but is in addition UV stable, non-toxic and non-endocrine disrupting.

In another embodiment the zinc oxide based formulation shows a sharp UV spectral absorption band edge at about 375 nm, which corresponds with the spectral optical band gap of pure zinc oxide.

In another embodiment cornstarch or arrowroot powder or both added to the zinc oxide based formulation increase UV absorption providing an additional SPF boost by reducing the number of pinholes when the zinc oxides based formulation is applied as a thin film and also improving the physiochemical bonding all the constituents in the formulation.

In another embodiment it has also been found that the addition of carrageen and aloe is useful in stabilizing the final formulations and improving film-forming properties.

BRIEF DESCRIPTION OF THE FIGURES

FIG. 1 illustrates, in graphical form the inadequacy in UVA and UVB stability of current SPF formulations. The plot is taken from the article entitled "In vitro assessments of UVA protection by popular sunscreens available in the United States," by Steven Q. Wang, M D, Joseph W. Stanfield, M S, and Uli Osterwalder, MSc, published by the Journal of American Academy of Dermatology on pages 934-942 in the December 2008 issue.

FIG. 2 graphically exhibits the results of using the zinc oxide dispersion in an SPF formulation with an SPF value of 111.6. The plot shows that the disclosed formulation remains stable at and effectively protects against exposure to UV wavelengths between about 290 nm and about 375 nm, a range that includes unsurpassed protection in the UVA regime. No known natural-based, earth-grown, Ecocert® certified SPF formulation is stable in that UV range, thereby providing unsurpassed skin protection without any toxicity.

FIG. 3 graphically represents results of in vitro testing of variations of the disclosed SPF formulations. These variations include one formulation made with B1 phase without a phosphatidylcholine such as Phospolipon® 90G supplied by American Lechithin Company in Oxford, Conn. (Curve A), one made with Phase B-II and phosphatidylcholine such as Phospolipon® 90G, Curve B, and a third with Phase B-II and a preparation of aloe and carrot oil, Curve C. The graph shows that each of the products provides unparalleled UVA and UVB stability.

DETAILED DESCRIPTION OF THE FIGURES

Figure 1:
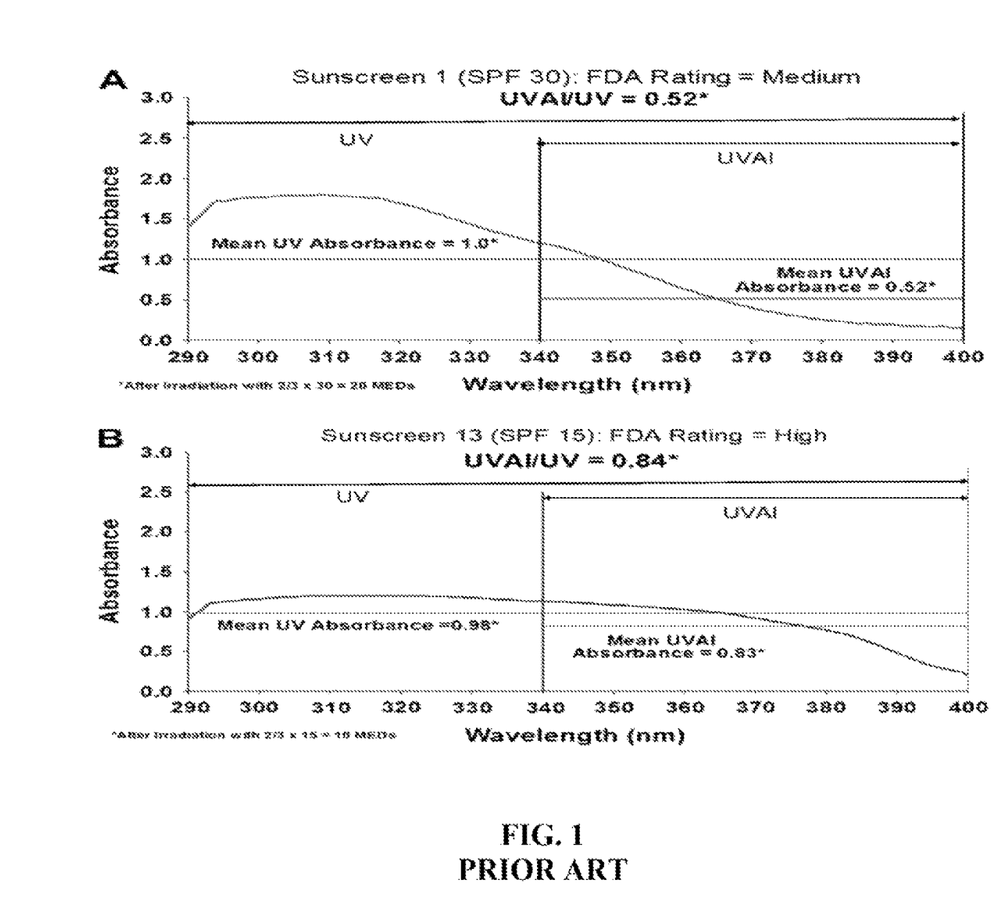

In FIG. 1, the data supplied for product A and resulting line plot indicates that a single sunscreen product with an SPF value of 30 does not remain stable at wavelengths above about 340 nm, and therefore does not provide the desired broad spectrum protection. The data supplied for product B and resulting line plot is a sunscreen product with an SPF value of 15 with improved UVA stability versus that of the first product but which begins to rapidly destabilize at a wavelength of about 360 nm.

Figure 2:
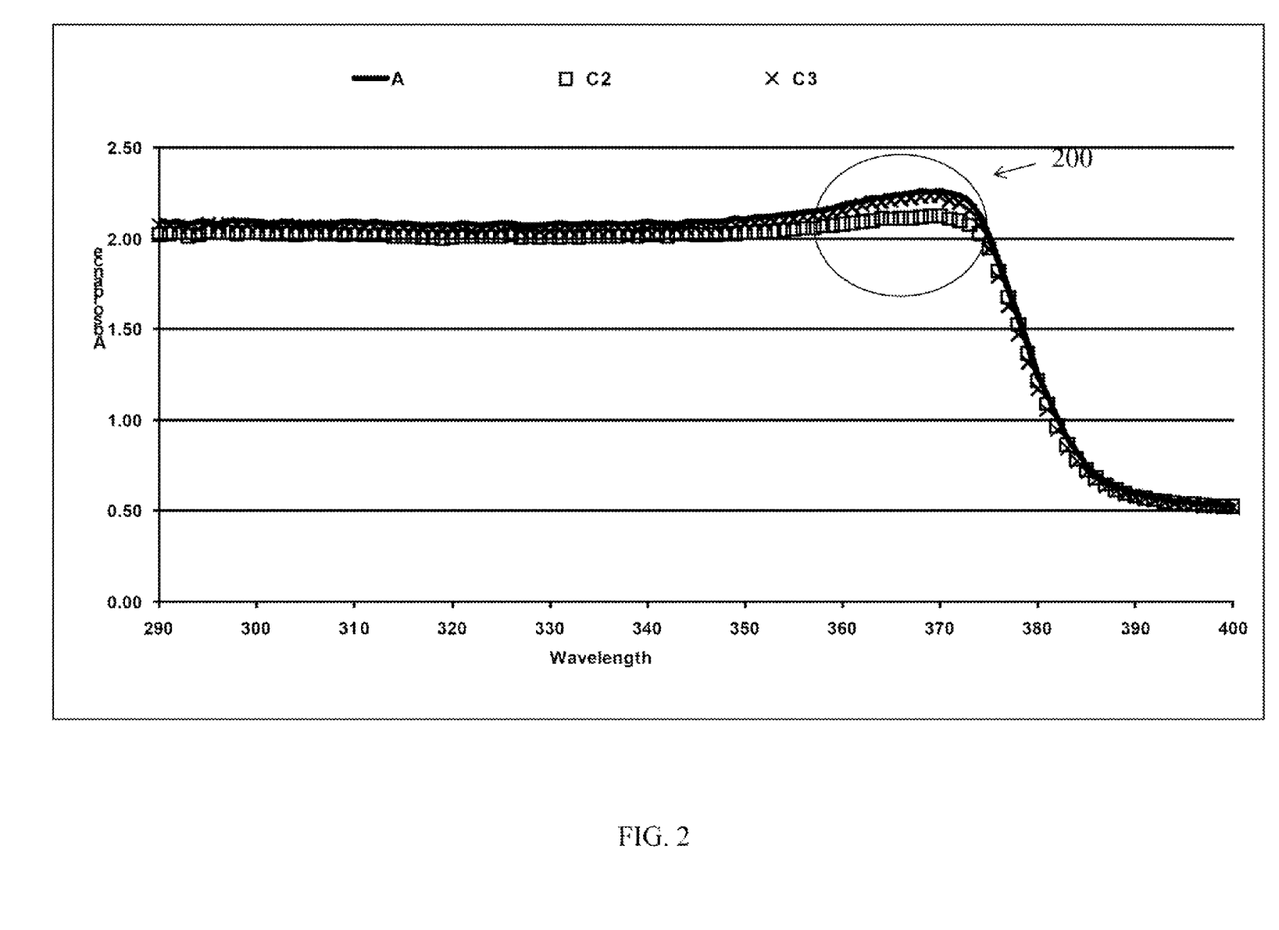

FIG. 2 clearly illustrates the efficaciousness of the disclosed formulations. Curve A represents an SPF formulation comprising 2.4 grams of cornstarch, 200 grams of the fully dispersed zinc oxide compound (80% by weight of the final formulation), and 16.5% by weight of Phase B and 3.21% of Phase C, made with 50 ml of carrot oil, 50 ml of glycerine, and 1 gram of lecithin, with an SPF value of 118.7. Curve C2 is an SPF formulation with 570 grams of the compound (70% by weight of the final formulation), 187.28 grams of Phase B (23%), 40.7 grams of Phase C (5.0%), and 16.28 grams of cornstarch (2%), as well as 5% by weight of carrot oil, with an SPF of 111.6. Curve C3 comprises the same components as in Curve C2 without the addition of cornstarch and with an SPF value of 102.2. The data indicates that SPF is increased by about 10% with the addition of about 2% by weight of cornstarch due to the production of an improved film with little or no pinholes. Feature 200 indicates a surprising result, namely that all of the variations of the formulation display increased absorbance in the UVA range from about 360 nm to about 375 nm.

Figure 3:
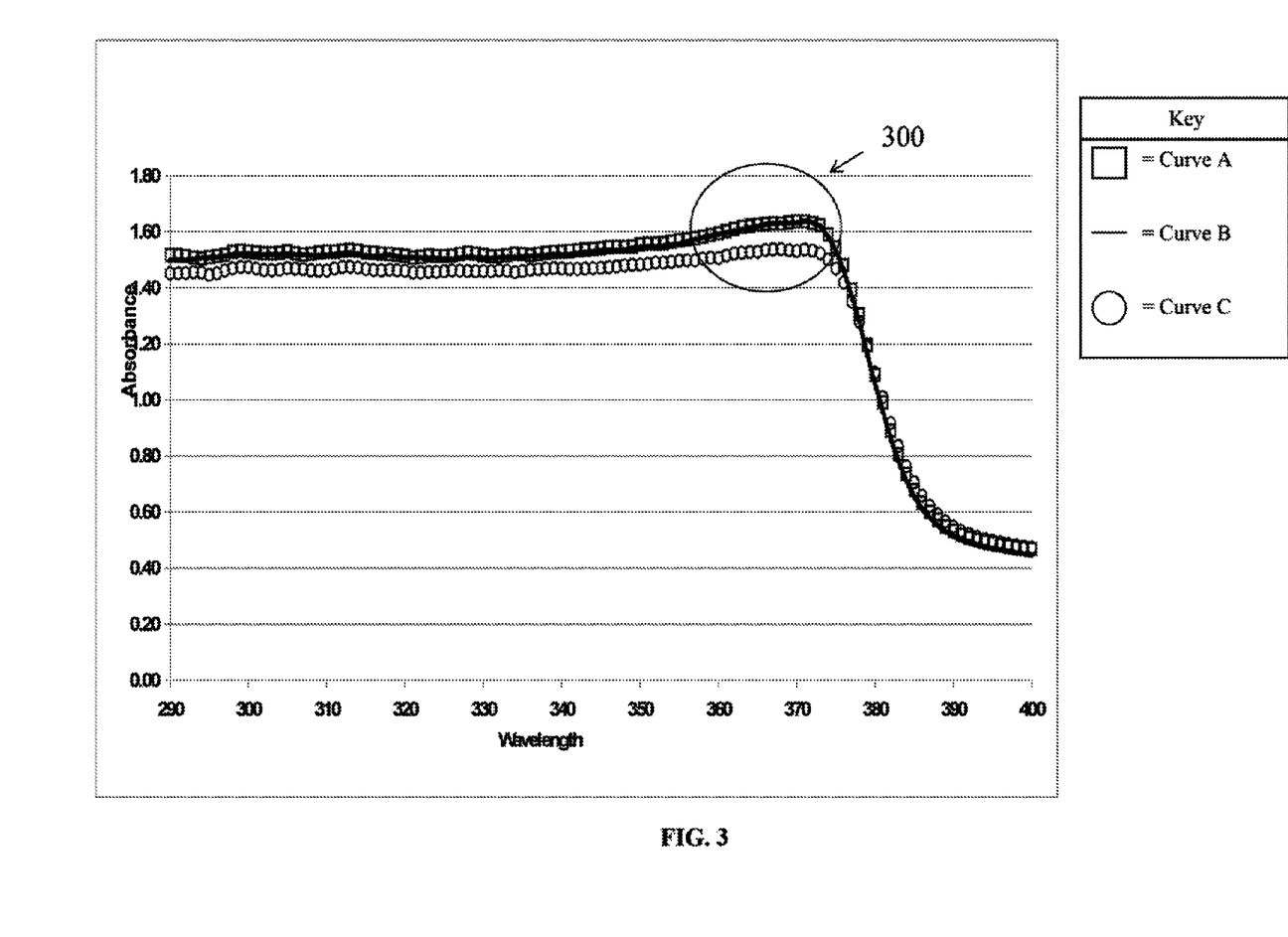

In FIG. 3, Curve A represents an SPF formulation with an in-vitro SPF value of 33.3 and represents a formulation with 38.8% by weight of zinc oxide compound G1309 and 38.8% by weight of a Phase B-I in this case using no phosphatidylcholine such as Phospolipon® 90G, which may be optionally, used an emulsifier. The formulation also included 9.71% by weight of glycerine, 9.71% by weight of Phase C, and 2.91% by weight of cornstarch. As the graph shows, this product performed reliably with UVA and UVB stability up to a wavelength of about 375 nm. Curve B represents an SPF formulation with an in-vitro SPF value of 32.7 using 41.67% by weight of zinc oxide compound G1309-2 and 37.6% by weight of a Phase B-2 including phosphatidylcholine such as Phospolipon® 90G as an emulsifier. Also used were 10.4% by weight of glycerine, 7.29% Phase C, and 3.02% cornstarch. This product also performed consistently with impressive and unparalleled UV stability. Curve C represents an SPF formulation with an in-vitro SPF value of 29.0 and represents 50% by weight of the same zinc oxide compound represented by Curve B, 12.5% glycerine, 7.5% Phase C, 3.0% cornstarch, and 27% by weight of Phase B-2 phase that, in this case, included an aloe and carrot oil preparation with 15.7% by weight of aloe and 0.97% carrot oil. Though this product has a lower SPF value than the other two, it nevertheless exhibited unprecedented UV stability at the longer UVA absorptions wavelengths. Feature [300] indicates the same surprising result; all of the variations of the formulation display increased absorbance in the UVA range from about 360 nm to about 375 nm.

Figure 4:
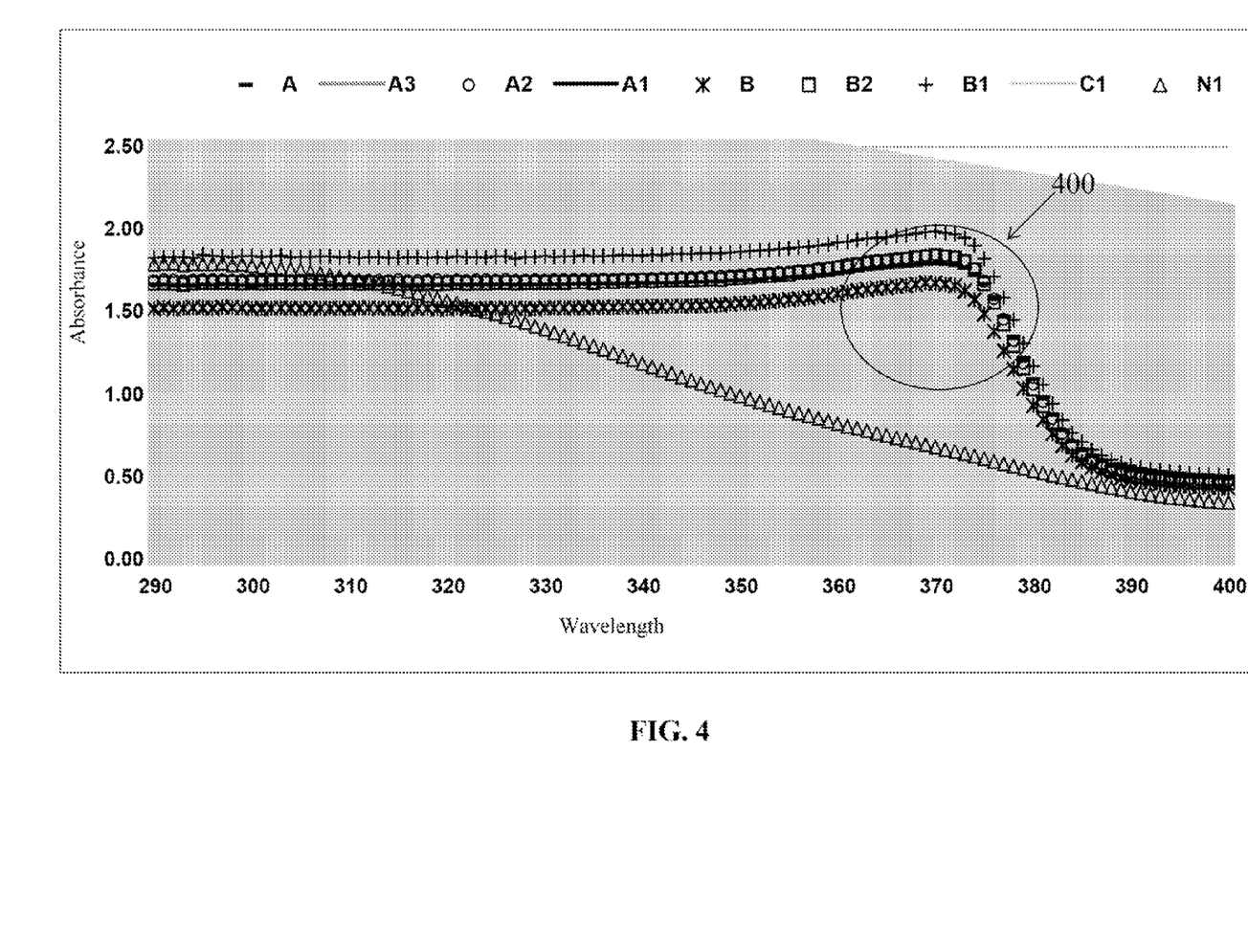
FIG. 4 graphically details a comparison of different versions of the formulation, differentiated by the inclusion or exclusion of cornstarch or arrowroot powder. Curve A represents a formulation made with B-IV phase, Curve A1 the formulation with arrowroot, Curve A2 with cornstarch, and Curve A3 without cornstarch. Curve B shows the results of a formulation made with Phase B-II, Curve B1 the formulation with arrowroot, and Curve B2 the formulation without cornstarch. Also shown are two control products, which display the uniqueness of the UVA and UVB stability provided by the disclosed formulation.

In FIG. 4, Curve A represents a formulation with an in-vitro SPF value of 45.5. This product included 200 grams, or 48.8% by weight, of the zinc oxide compound (internal control number G1309-2) and 33.7% by weight of a Phase B-IV that included only 93.7% glycerine, 5.3% olive oil, and 0.99% arrowroot powder. Curve B shows the absorbance of a product with an SPF value of 32.9 made with 60.1% G1309-2 zinc oxide compound and 19.9% of a Phase B-II, which utilized 5.2% rice bran oil, 0.25% orange wax, and 0.15% beeswax along with 93.3% glycerine and 1.04% arrowroot powder. Curve A1 exhibits the data from a formulation with an SPF of 61.7 and the addition of 4.25% by weight of arrowroot, while Curve A2 with an SPF value of 48.5 and Curve A3 with an SPF value of 42.5 show formulations with and without 4.25% by weight of cornstarch, respectively. This illustrates that cornstarch provides an increase in SPF of about 10% due to the production of a pinhole free film. It also indicates another surprising results, that the arrowroot powder raises the SPF even more significantly. In this case the cause of the SPF boost is suspected to be improved physiochemical bonding of the components. Curve B1 represents a formulation with 3.0% arrowroot and an SPF of 66.8, and Curve B2 shows a similar formulation without the addition of any cornstarch or arrowroot and an SPF of 46.6. Thus, these samples support the assertion that both cornstarch and arrowroot have a significant and positive effect on SPF using the SPF formulations of the present invention. Also shown in the graph is the data for two control products: Caribbean Solutions Natural Skin Care®, Curve C1 and Neutrogena Sensitive Skin® Sunblock Lotion, Curve N1. The samples provided have SPF values of 28.7 and 39.0, respectively. These particular commercial products were chosen because they represent the available products in which inorganic substances are the primary active ingredients. Clearly, these products do not provide the enhanced UVA and UVB stability and protection provided by the present application; their absorbance rates begin to decline rapidly at about 325 nm. Again, Feature 400 indicates the surprising result that all of the variations of the formulations of the present application display increased absorbance in the UVA range from about 360 nm to about 375 nm.

INCI lists for the commercial products are provided below:
Caribbean Solutions Natural Skin Care®:
Active Ingredients: titanium dioxide (9.5%) and zinc oxide (3.5%)
Inactive Ingredients: organic aloe leaf, wild pansy, green coffee bean extract, hibiscus, cucumber, sunflower, essential oil essence.

Figure 5:
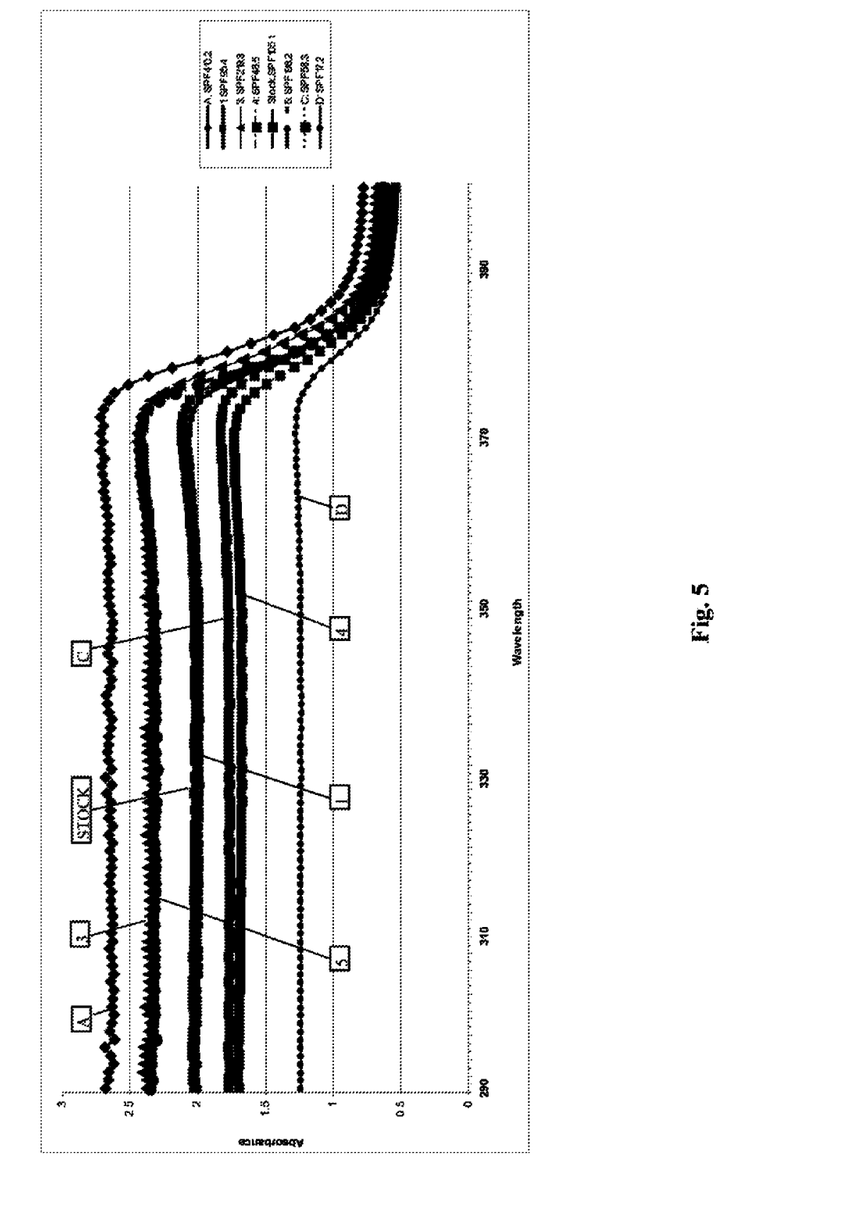
FIG. 5 graphically displays the absorption spectrum of variations of the zinc oxide complex. Curve [A] and Curve [1] show the data for the same variation of the zinc oxide complex made in two different facilities with Emuglade® PL 68/50. Curve [3] and Curve [C] represent the data for the zinc oxide complex stabilized with Emuglade® PL 68/50 and glycerine, and in Curve [4] and Curve [D], the data for a zinc oxide complex stabilized with Emuglade® PL 68/50, glycerine, and Eumulgin® SG. Curve [Stock] shows a stock solution of the zinc oxide complex that was not dried, and Curve [5] illustrates the absorption ability of a zinc oxide complex made with glycerine only. All variations displayed impressive and unparalled UVA/UVB stability from about 290 nm to about 375 nm wavelength of light.

Neutrogena Sun-block Lotion Sensitive Skin®
   Active Ingredients: titanium dioxide (9.1%)
      Inactive Ingredients: water, C12 15 alkyl benzoate, neopentyl glycol dioctanoate, glycerine, potassium cetyl phosphate, isopropyl C12 15 pareth 9 carboxylate, cetyl alcohol, phenoxyethanol, steareth 21, tocopherol, calcium pantothenate, camellia oleifera, extract, panthenol, BHT, neopentyl glycol diisostearate, aluminum hydroxide, iron hydroxide, steareth 2, stearic scid, trimethylolpropane triethylhexanoate, acrylates/C10 30 alkyl acrylate crosspolymer, disodium EDTA, carbomer, butylene glycol, triethanolamine, butylparaben, methylparaben, isopropylparaben, isobutylparaben In FIG. 5, Curve [A] and Curve [1] illustrate the data for an identical variation of the zinc oxide complex produced in two different facilities/laboratories. The samples included 1% by weight of Emuglade® PL 68/50 as an emulsifier. The difference in data between the two samples is a result of the difference in the process used to finalize the product(s). Curve [A] shows the zinc oxide complex with an SPF value of 410.2, while Curve [1] represents the same zinc oxide complex with an SPF value of 95.4, processed slightly differently. Curve [3] and Curve [C] provide data for a zinc oxide complex with an SPF value in the range between about 58.3 and about 219.3 that was stabilized with 1% by weight of both glycerine and Emuglade® PL 68/50. Curve [4] and Curve [D] illustrate the results of a zinc oxide complex that was treated with 1% by weight of glycerine, Emuglade® PL 68/50, and sodium stearoyl glutamate such as Eumulgin® SG. The addition of Eumulgin® SG, in this case, it is reasoned, reduced the efficacy of the zinc oxide complex by destabilizing the zinc oxide complex as Eumulgin® SG is a salt that tends to reduce the emulsion strength in some compositions. Curve [5] represents the data for a zinc oxide complex with about 2.0% to about 3.5% by weight of glycerine, an addition that produced an SPF value of 198.2 and a product that performed similarly to the product represented by Curve [3]. In all of the above samples, the zinc oxide complex was dried following a 24-hour period during which the zinc oxide complex was kept at or above a pH of 10. However, the stock solution represented by Curve [Stock] is a sample of the zinc oxide complex in a liquid/paste form which provides an initial SPF value of 105. This complex includes 1% by weight each of Emuglade® PL 68/50 and Eumulgin® SG and produces a zinc oxide precipitate in the form of a creamy white paste. Because excess ammonia was not removed from this variation of the complex, and because Eumulgin® SG destabilizes the complex producing salts and water within the emulsion, this version of the complex proved to be highly unstable and thus not as desirable as the other variations displayed in FIG. 5.

DETAILED DESCRIPTION OF THE INVENTION

The zinc oxide complex disclosed is a new composition of matter with unparalleled UVA and UVB spectral absorption stability displaying high SPF values as well as improved heat absorption, water resistance and insulation characteristics. The process for making the zinc oxide complex involves adding a common buffering agent, such as ammonium hydroxide, sodium hydroxide, or other amine-based compositions or amino acids such as L-arginine, to basic distilled water and buffering the water to a pH of 10 or greater. It is critical that the pH of the solution remain above 10 to prevent the formation of zinc hydroxide, which can result in significant physiochemical destabilization of the zinc oxide complex. Micronized particles of zinc oxide with typical diameters of, for example, about 0.1 micron (um) to greater than 0.9 um, are added to the buffered water and it may be necessary to add the buffering agent and the zinc oxide alternatively to ensure that the pH remains between about 10 and about 11. The zinc oxide complex, within 24 hours normally increases in pH from about 10.0 to about 10.4 or greater. The zinc oxide complex should be allowed to sit overnight to undergo the reaction at a temperature of between about 4 degrees and about 20 degrees centigrade. At this point, the zinc oxide complex already exhibits UVA and UVB absorption stability.

After 24 hours, the complex may be dried and rinsed with an aqueous solution, buffered with, for example, sodium bicarbonate allowing for formation of a semi-solid, cake-like consistency. Drying the product ensures that excess ammonia or other pH buffering solutions remaining in either the gaseous or liquid form is removed. This technique helps to ensure that the zinc oxide complex remains as a stable product. To further stabilize the product, placement of the zinc oxide complex into an emulsifier and/or an emollient is desired. Glycerine is an emollient that may be used and has been found to enhance the UVA/UVB spectral absorption stability of the product. Additionally, an emulsifier, such as Emuglade® PL 68/50, a composition of cetearyl alcohol and cetearyl glucoside obtained from the Cognis Corporation, sodium stearoyl glutamate such as Eumulgin® SG supplied by Cognis Corporation, cetearyl glucoside such as TEGO® Care CG 90 supplied by Evonik Industries AG or other glucoside, can be added to the zinc oxide complex. These glucosides also provide the zinc oxide complex with physiochemical stability and can raise the pH of the zinc oxide complex once again, further preventing zinc hydroxide formation. Though glycerine may be added without applying heat, the emulsifiers described may be added with the addition of heat to either the emulsifier or the zinc oxide complex. Either the emulsifiers may be preheated to between about 60 degrees and about 100 degrees centigrade and subsequently added to the zinc oxide complex, or the zinc oxide complex may be heated to between about 60 degrees and about 100 degrees centigrade before adding emulsifier.

Zinc oxide is a hexavalent molecule, that is, it has six available bonding sites. One theory is that in order to stabilize zinc oxide and to enhance its ability to absorb and reflect ultraviolet radiation, every potential bonding site should be stabilized during the reaction. The present disclosure provides a preferred embodiment where these bonding sites be filled with ammonium; however, it is possible to use other amine based compounds such as L-arginine, instead. The chemical formula for L-arginine is $C_6H_{12}N_4O_2$. L-arginine is an amino acid with a 4 carbon aliphatic straight chain as the amino acid side chain capped with a guanidinium group at the distal end. It is the guanidinium group that imparts basic properties to L-arginine, thus allowing it to be used in place of ammonium hydroxide to buffer the pH of the distilled water to 10 or greater. Furthermore, L-arginine should be able to fill the six bonding sites of zinc oxide, albeit it with more stearic hindrance, thus providing for a zinc oxide complex with L-arginine instead of ammonium hydroxide.

Sun-block formulations generally contain organic sunscreens and inorganic sun-blocking agents, such as zinc oxide. In distilled water with a pH of about 7.0, however, zinc oxide undergoes an immediate reaction and is converted to zinc hydroxide, which destabilizes any composition in which the zinc oxide is dispersed. Coating micronized zinc oxide with silicone oil or surface treating are two methods of stabilizing the zinc oxide; however, both treatments are considered synthetic components and neither is fully adequate in that not all of the zinc oxide surface can be perfectly and completely coated. It was found that untreated zinc oxide could be stabilized in a composition by raising the pH using buffered water and specifically water buffered with ammonium hydroxide ($NH_4OH$). Once the pH is increased and kept between about 9.5 and about 11.0, the production of zinc hydroxide is minimized and zinc oxide remains stable. Once the stability issue is resolved, a resultant dispersion was completed using a glycerine base. SPF formulations utilizing the full zinc oxide dispersion were then completed and tested, in vitro, for SPF value. The Labsphere UV 2000S Ultraviolet Transmittance Analyzer, available from Labsphere of North Sutton, NH is a device that calculates SPF value, UVA to UVB ratio, and critical wavelength for a given sample, and was used in this case to determine the SPF value of the complex. Surprisingly, at least one zinc oxide based dispersion provided an SPF value of 457.

The zinc oxide based dispersion is produced through a reaction of the zinc oxide with alkaline buffered, distilled water at a pH greater than about 10.0. The dispersion is allowed to sit for about 24 hours at a temperature of between about 4 and about 20 degrees centigrade and produces a zinc oxide dispersion that must be further processed to produce the fully dispersed zinc oxide compound disclosed. Placement into an emollient, such as glycerine, and/or an emulsifier, such as EMUGLADE® PL 68/50 or sodium stearoyl glutamate, such as EUMULGIN® SG, is required and may or may not be preceded by a process of drying and rinsing. Once the fully dispersed compound is available, the compound may be used in any SPF protective formulation.

A pelletized emulsifier such as EMUGLADE® PL 68/50, a mixture of cetearyl alcohol and cetearyl glucoside, obtained from Cognis Corporation, was added to the zinc oxide dispersion for sun block applications. Additionally and alternatively dispersion formulations included the use of TEGOSOFT® cetearyl polyglucoside, obtained from Evonik, in lieu of EMUGLADE® PL 68/50. One effect of sodium stearoyl glutamate such as EUMULGIN® SG or cetearyl glucoside and cetearyl alcohol such as EMUGLADE® PL 68/50 or cetearyl glucoside or cetearyl polyglucoside is to raise the pH of the dispersion again, avoiding zinc hydroxide formation.

When glycerine is added to the buffered water zinc oxide mixture and emulsifier dispersion it renders a film forming complex that has a smooth, tactile feel. The use of glycerine also has been found to add some SPF boosting properties, but only when added under certain conditions. The conditions occur when the glycerine is added to the dried semi-solid zinc oxide dispersion with or without the added emulsifier. Additionally it was found that the addition of sodium stearoyl glutamate such as EUMULGIN® SG, without the addition of glycerine, could destabilize the dispersion or compound by forming salts and water. The destabilization manifests itself as bubbles, creating pinholes in the film formed when squeezing this compound between microscope slides, which in turn reduces SPF values.

Glycerine has also been added to the dried semi-solid zinc oxide and buffered water dispersion without the emulsifier and been found to be stable, especially when adding oils. It was found that the glycerine assisted the oils to mix into the dispersion creating a compound, where adding the oils before the glycerine would render the dispersion unstable. Stability in this manner, allows for the addition of gamma oryzinol or rice bran oil, which is also known to be a natural SPF booster. It was also found that when glycerine is added at room temperature, it may increase the SPF when the dispersion or compound is developed under the proper conditions, as described above.

Sunblock formulations of the present application also benefit from the addition of aloe and oils to the active ingredients. It has been found that the aloe and oils must be added separately to the ZnO dispersion of the present application. Generally, aloe is an acidic substance with a pH between about 3.5 and about 4.5. To ensure that the basic dispersion does not destabilize upon the addition of aloe, the aloe used must be at a pH of at least 9.0 before it is added to the dispersion or to any oils in providing an SPF formulation. The pH of the aloe can be increased to at least 9.0 through the addition of L-arginine. L-Arginine is an amino acid that has been determined to help stabilize inactive components added to the zinc oxide dispersions and compounds of the present application.

A prospective INCI list comprises:
zinc oxide
distilled buffered water
glycerine
aribinogalacatan
vitamins E and C
emulsifier—including cetearyl glucoside and/or phosphatidyl choline
oils including essential oils—raspberry seed oil, avocado oil, olive oil, jojoba oil, carrot oil, rice bran oil, etc.
gamma oryzinol
waxes—such as bees wax and orange peel wax
cornstarch or arrowroot powder
frankincense
rosemary
colloidal silver (as a anti-microbial agent)

Examples for the Preparation of the Zinc Oxide Complex

The examples shown below provide variations of the zinc oxide complex described above.

The following is a method for manufacturing a UVA and UVB stable zinc oxide complex from natural-based, earth-derived ingredients:

Example I

1. In a container add distilled water.
2. Add/mix $NH_4OH$ into the distilled water to make a buffered water solution until the pH of the mixture is between 10 and 11.
3. Add/mix micronized zinc oxide particles to the mixture monitoring the pH to ensure it is maintained between 10 and 11.

Allow mixture to react.

If pH falls below 10, add mixture of distilled water and $NH_4OH$ to raise pH between 10 and 11.

4. Let mixture sit for 24 hours at a temperature of between 4 and 20 degrees centigrade.
5. Heat emulsifier to between 60 and 100 degrees centigrade for up to 30 minutes.
6. Emulsifier may be one of several including but not limited to; Emuglade® PL 68/50, supplied by Cognis Corporation, which is comprised of cetearyl alcohol and cetearyl glucoside or cetearyl glucoside such as TEGO® Care CG 90 supplied by Evonik Industries AG and Phospolipon® 90G supplied by American Lechithin Company in Oxford, Conn.

Add emulsifier to mixture at between 0.1% and 5% by weight of the mixture.

Example II

1. In a container add distilled water.
2. Add/mix NH$_4$OH into the distilled water until the pH of the mixture is between 10 and 11.
3. Add/mix micronized zinc oxide to the mixture monitoring the pH to ensure the pH is maintained between 10 and 11.
   Allow mixture to react.
   If pH falls below 10, add mixture of distilled water and NH$_4$OH to raise pH to between 10 and 11.
4. Let mixture sit for 24 hours at a temperature of between 4 and 20 degrees centigrade.
5. Add 1% by weight of glycerine to the zinc oxide complex.
6. Heat emulsifier to between 60 and 100 degrees centigrade for up to 30 minutes.
   Emulsifier used is TEGO® Care CG 90 cetearyl glucoside.
7. Add 0.1% to 5% by weight emulsifier to mixture.

Example III

1. In a container add distilled water.
2. Add/mix NH$_4$OH into the distilled water until the pH of the mixture is within range of between 10 and 11.
3. Add/mix micronized zinc oxide to the mixture monitoring the pH to ensure the pH is maintained between 10 and 11.
   Allow mixture to react.
   If pH falls below 10, add mixture of distilled water and NH$_4$OH to raise pH to between 10 and 11.
4. Let mixture sit for 24 hours at a temperature of between 4 and 20 degrees centigrade.
5. Heat emulsifier to between 60 and 100 degrees centigrade for up to 30 minutes.
   Emulsifier may either be Emuglade® PL 68/50, comprised of cetearyl alcohol and cetearyl glucoside or cetearyl glucoside such as TEGO® Care CG 90.
6. Add emulsifier to mixture at between 0.1% and 5% by weight.
   Add 0.5% to 3% by weight of sodium stearoyl glutamate such as Eumulgin® SG supplied by Cognis Corporation and 1% by weight glycerine.

Example IV

1. In a container add distilled water.
2. Add/mix NH$_4$OH into the distilled water until the pH of the mixture is between 10 and 11.
3. Add/mix micronized zinc oxide to the mixture monitoring the pH to ensure the pH is maintained between 10 and 11.
   Allow mixture to react.
   If pH falls below 10, add mixture of distilled water and NH$_4$OH to raise pH between 10 and 11.
4. Let mixture sit for 24 hours at a temperature of between 4 and 20 degrees centigrade.
5. Heat emulsifier to between 60 and 100 degrees centigrade for up to 30 minutes.
   Emulsifier used is cetearyl glucoside as TEGO® Care CG 90.
6. Add emulsifier to mixture at 0.1% and 5% by weight of the mixture.
   Add 0.5% to 3% by weight sodium stearoyl glutamate such as Eumulgin® SG.

Example V a. In a container add distilled water.
b. Add/mix NH$_4$OH into the distilled water until the pH is between 10 and 11.
c. Add/mix micronized zinc oxide particles to the mixture monitoring the pH to ensure the pH is maintained between 10 and 11.
   Allow mixture to react.
   If pH falls below 10, add mixture of distilled water and NH$_4$OH to raise pH to between 10 and 11.
d. Let mixture sit for 24 hours at a temperature between 4 and 20 degrees centigrade.
e. Heat the mixture to between 60 and 100 degrees centigrade and add 1% by weight of Emuglade® PL 68/50, supplied by Cognis Corporation.
   Mix.
f. Allow for the mixture to cool.

In all cases for examples I-V above the NH4OH can be substituted with NaOH or L-Arginine to accomplish the same pH requirement and ultimately a stable ZnO complex.

Example VI (to make the zinc oxide stock complex)
1. In a container add 983 grams of distilled water with a pH of 6.2.
2. Add/mix dilute NH$_4$OH into the distilled water until the pH of the mixture is 7.1.
3. Add/mix 453.2 g zinc oxide with water. The mixture has a pH of 7.6.
4. Add/mix 40 drops NH$_4$OH to raise pH to 10.4.
5. Add/mix additional 79.9 g of zinc oxide. The mixture has a pH of 10.3.
6. Add/mix 333 grams of water. The final pH of the zinc oxide complex is 10.4.
7. Add 0.5% to 3% by weight of sodium stearoyl glutamate such as Eumulgin® SG and a combination of cetearyl alcohol and cetearyl glucoside such as Emuglade® PL 68/50. The SPF value of this product is 68.
8. Left to stabilize for 3 months, the SPF value is 457, though it will degrade to an SPF value of 105.1 within 60 days.

Example VII (to make a variation of the zinc oxide stock complex)
1. In a container, add 983 g of distilled water with a pH between 6.8 and 7.2.
2. Add 453.2 grams zinc oxide and mix with water.
3. Add an additional 79.9 grams zinc oxide to the water, and mix well.
4. Add 60 drops of NH$_4$OH until the pH of the mixture is 10.7.
5. Add/mix 333.2 g distilled water. The mixture has a pH of 10.6.
6. Add 11 drops of NH$_4$OH until the pH of the mixture is 10.4.
7. Mix the solution. The final pH is 10.6. After shaking, to ensure homogeneity of the solution, the SPF value of the solution is 33.
8. Add 33.25 g sodium stearoyl glutamate such as Eumulgin® SG. The mixture has a pH of 11.44.
9. Mix the zinc oxide complex for 15 minutes, and heat the zinc oxide complex to 70 degrees centigrade. The zinc oxide complex now has a pH of 9.98.

10. Add 1% by weight a combination of cetearyl alcohol and cetearyl glucoside such as Emuglade® PL 68/50, and mix for 10 minutes.

11. Remove the zinc oxide complex from heat and add 1% by weight of glycerine.

12. Mix and leave zinc oxide complex to cool for 2 hours, then cover. The final pH is 10.

Example for SPF Formulations

Examples of the complex and natural sun block formulations are shown below.

The following is the method for manufacturing an all natural-based ingredient, Ecocert® certified, zinc oxide based compound with inherent, unsurpassed UVA and UVB stability:

Example VIII

1) Mix 200 grams zinc oxide dispersion and 50 grams glycerine.
2) Add 50 grams Phase C prepared as follows:
  a. Mix 0.75 grams Phospolipon® 90G into 100 ml glycerine and heat to 130 degrees centigrade. Allow to cool.
  b. Add 100 ml carrot oil.
3) Add 200 grams Phase B-I prepared as follows:
  a. Mix 1886 grams glycerine and 106 grams rice bran oil.
  b. Melt 5 grams orange wax and 3 grams beeswax and add to mixture.
  c. Homogenize.
4) Add 15 grams of cornstarch, and mix.
5) Allow product to rest.
6) Homogenize for 2-3 minutes.

Example VIX

1) Mix 200 grams zinc oxide dispersion and 50 grams glycerine.
2) Add 35 grams Phase C prepared as described in Example 1.
3) Add 180.5 grams B-II phase prepared as follows:
  a. Mix 1786 grams glycerine, 106 grams rice bran oil, 5 grams orange wax, and 3 grams beeswax (waxes should not be pre-melted).
  b. Mix 6.75 grams phosphatidylcholine such as Phospolipon® 90G into 93.25 grams glycerine and heat to 130 degrees centigrade.
  c. Add this combination (b) to (1), (2), and (3) above and mix.
  d. Allow to cool and homogenize.
4) Add 14.5 grams cornstarch, and mix.
5) Allow product to rest.
6) Homogenize 2-3 minutes.

Example X

1) Mix 200 grams zinc oxide dispersion and 50 grams glycerine.
2) Add 30 grams C phase as described in Example I above:
  a. Mix 10 grams Phospolipon® 90G into 100 grams glycerine and heat to 130 degrees centigrade.
  b. Add this mixture to 320 grams Phase B-II, containing 81 grams aloe with L-arginine and 5 grams carrot oil.
  c. Mix and homogenize.
3) Add 12 grams cornstarch and mix.
4) Allow product to rest.
5) Homogenize for 2-3 minutes.

Example XI

1) Add 60 grams Phase C as described in Example 1 to 200 grams zinc oxide dispersion:
  a. Mix 80 ml glycerine and 3 grams Phospolipon® 90G and heat to 92 degrees centigrade.
  b. Add this to 320 ml glycerine and mix well.
  c. Add 100 ml carrot oil.
  d. Mix the mixture and homogenize, then allow to rest.
  e. Remix after resting period, slowly.
2) Add 138 grams Phase B-IV:
  a. Mix 471.5 grams glycerine, 26.5 grams olive oil and 5 grams arrowroot.
  b. Homogenize.
3) Add 17 grams arrowroot and mix.

Example XII

1) Add 40 grams C phase, as described in Example 1 to 200 grams zinc oxide dispersion and mix.
2) Add 20 grams glycerine and mix.
3) Add 66.5 grams Phase B-II, and mix well:
  a. Mix 943 grams glycerine, 53 grams rice bran oil, and 10.5 grams arrowroot.
  b. Melt 2.5 grams orange wax and 1.5 grams beeswax into the mixture.
4) Add 6.5 grams arrowroot, and mix.

Example XIII

1) Add 40 grams Phase C phase, as described in Example 1 to 200 grams zinc oxide dispersion.
2) Add 17 grams glycerine.
3) Add 131 grams Phase B-I:
  a. Heat 472.25 grams glycerine to 65 degrees centigrade.
  b. Add 5 grams TEGOSOFT® or cetearyl glucoside to the heated glycerine.
  c. Add to this mixture 26.75 grams rice bran oil with 0.535 grams L-arginine that has been mixed, heated, and mixed again, 0.625 grams orange wax, and 0.375 grams beeswax.
  d. Mix well for 5-10 minutes and then homogenize for 10 minutes, 5 at full speed, and then mix slowly for less than 5 minutes.

Example XIV

1) Follow the procedure as outlined in EXAMPLE VI.
2) Add 5.5 grams arrowroot and mix.

Example XV

1) Follow the procedure as outlined in EXAMPLE VI.
2) Add 5.5 grams cornstarch and mix.

Example XVI

1) Add 40 grams Phase C as described in Example 1 to 200 grams zinc oxide dispersion.
2) Add 17 grams glycerine
3) Add 131 grams Phase B-II:
  a. Heat 472.25 grams glycerine to 65 degrees centigrade.
  b. Add 5 grams EMUGLADE® PL 68/50 and mix until the pellets melt.

c. Add 0.625 grams orange wax and 0.375 grams beeswax, and allow to melt.
d. Add 26.75 grams rice bran oil without L-arginine.
e. Mix well for 5-10 minutes and then homogenize for 10 minutes, 5 at full speed, and then mix slowly for less than 5 minutes.

Example XVII

1) Follow the procedure outlined in EXAMPLE IX.
2) Add 12 grams arrowroot and mix.

Example XVIII

1) Add to 200 grams zinc oxide dispersion, 8 grams Phase C:
  a. Mix 50 ml carrot oil, 50 ml glycerine and 1 gram Phospholipon® 90G for 5 minutes.
  b. The resulting mixture should have a pH of 6.5.
2) Add 41 grams Phase B and mix:
  a. Mix 1886 grams glycerine with 106 grams rice bran oil.
  b. Melt 5 grams orange wax and 3 grams beeswax, and add to mixture.
  c. Homogenize.
3) Add 2.4 grams cornstarch and mix.

Example XIX

1) Add 187.28 grams Phase B, as described above, to 570 grams of zinc oxide dispersion, which should be 3.48% by weight glycerine.
2) Add 40.7 grams Phase C, as described above and mix.

Example XX

1) Follow the procedure outlined in EXAMPLE XII.
2) Add 16.28 grams cornstarch and mix.

Example XXI

1. Add 5% by weight of Antaron Ganex® to CVS Sensitive Skin Sunblock Lotion.
2. Blend well.
3. Measure the in-vitro SPF using Labsphere UV 2000S Ultraviolet Transmittance Analyzer and compare with the neat version of CVS Sensitive Skin Sunblock.
4. The SPF increases by about 6.25% from SPF value of 32.0 (CVS Sensitive Skin Sunblock Lotion neat) to SPF value 34.3 with the addition of 5% Antaron Ganex®.

Example XXII

1. Add 5% by weight of zinc oxide based dispersion mixed with 3.5% by weight glycerine to CVS Sensitive Skin Sunblock Lotion.
2. Blend well.
3. Measure the in-vitro SPF values using Labsphere UV 2000S Ultraviolet Transmittance
Analyzer and compare with the neat version of CVS Sensitive Skin Sunblock. The SPF values increases by about 47% from a SPF value of 32.0 for CVS Sensitive Skin Sunblock Lotin (neat) to a SPF value of 47.1 with the addition of zinc oxide based dispersion mixed with glycerine.

What is claimed is:

1. A composition of matter comprising zinc oxide particles, distilled water, and a pH-increasing buffering agent, which combined, is a chelated zinc oxide complex wherein said complex exhibits stable UVA and UVB spectral absorption between about 290 nm and about 375 nm wavelengths of light, wherein said buffering agent is selected from the group consisting essentially of L-arginine, sodium hydroxide, and ammonium hydroxide, wherein said zinc complex provides a moisture, perspiration and water-resistant barrier that is free of endocrine disrupters, and wherein said composition of matter into which the zinc oxide complex is incorporated is selected from the group consisting of a sunscreen, body care, and cosmetic product.

2. The composition of matter of claim 1, wherein said zinc oxide complex is dried and rinsed to form a creamy white paste, a semi-solid white cake-like consistency or a solid white powder/block.

3. The composition of matter of claim 1, wherein an emollient is added to said zinc oxide complex.

4. The composition of matter of claim 1, wherein said emollient is glycerine.

5. The composition of matter of claim 1, wherein an emulsifier is added to said zinc oxide complex.

6. The composition of matter of claim 1, wherein one or more emulsifiers and one or more emollients are added to said zinc oxide complex.

7. The composition of matter of claim 6, wherein said emulsifiers are selected from the group consisting of cetearyl alcohol, cetearyl glucoside, sodium stearoyl glutamate, or combinations thereof.

8. The composition of matter of claim 7, wherein said emulsifiers are any combination of cetearyl alcohol and cetearyl glucoside.

9. The composition of matter of claim 6, wherein said one or more emulsifiers are at least one glucoside emulsifier selected from the group consisting of cocoyl glucoside, cocoyl glucoside/cetearyl alcohol, cocoyl ethyl glucoside, disodium coco-glucoside citrate, lauryl glucoside, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or mixtures thereof.

10. The composition of matter of claim 6, wherein said one or more emulsifiers are selected from the group consisting of butylated PVP, cetyl alcohol, sodium acrylate/sodium acryloyldimethyltaurate copolymer, diethylhexyl naphthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6-hexaricinolate, polyglyceryl-4-oleate, polyglyceryl-4-oleate/PEG-8 propylene glycol cocoate, oleamide DEA, sodium glyceryl oleate phosphate, hydrogenated vegetable glyceride phosphates, or mixtures thereof.

11. The composition of matter of claim 6, wherein said one or more emulsifiers are selected from the group consisting of sodium stearoyl glutamate, dioctyldodecyl stearoyl glutamate, TEA-cocoyl glutamate, TEA-lauryl glutamate, TEA-stearoyl glutamate, aluminum stearoyl glutamate, monosodium glutamate, disodium glutamate, or mixtures thereof.

12. The composition of matter of claim 1, wherein carrot oil is added to said zinc oxide complex.

13. The composition of matter of claim 6, wherein the addition of said emulsifiers and/or said emollients improve the physiochemical stability of said zinc oxide complex.

14. The composition of matter of claim 6, wherein mixing and blending characteristics of said zinc oxide complex into materials can be controlled and/or adjusted by using different emulsifiers during mixing.

15. The composition of matter of claim 6, wherein said one or more emulsifiers are selected from the group consisting of cetearyl alcohol, cetearyl glucoside, sodium stearoyl glutamate, or mixtures thereof.

16. The composition of matter of claim 1, wherein said zinc oxide complex reflects or absorbs all UVB radiation from about 290 nm to about 320 nm and all UVA radiation from about 320 nm to about 370 nm without degradation in the spectral absorption.

17. The composition of matter of claim 1, wherein the anti-microbial properties of said zinc oxide complex are imparted into any organic or inorganic material.

18. The composition of matter of claim 1, wherein said zinc oxide complex provided in a paste or dried powder form functions as a UV spectral absorption stabilizing component for any organic or inorganic material.

19. The composition of matter of claim 1, wherein said zinc oxide complex provided in said paste or dried powder form is used in lieu of or together with other UVA/UVB stabilizing compounds and/or as an alternative or addition to carbon black.

20. The composition of matter of claim 1, wherein the degree of the water-resistant properties of said zinc oxide complex is adjusted by use of different emulsifiers.

21. A process for preparing the composition of matter of claim 1 comprising preparing a zinc oxide complex composition comprising the steps of:
   i. adding a buffering agent to distilled water in an amount effective to achieve a pH for the solution between 10.0 and about 11.0, selected from the group consisting essentially of L-arginine, sodium hydroxide, and ammonium hydroxide;
   ii. adding zinc oxide particles to the buffered distilled water solution while maintaining a pH between 10.0 and about 11.0; and
   iii. allowing the formed zinc oxide complex to react for about 24 hours at a temperature ranging from about 4° C. to about 20° C.

22. The process of claim 21, wherein said buffered water solution is prepared with ammonium hydroxide and distilled water.

23. The process of claim 21, further comprising drying and rinsing said zinc oxide complex following about 24 hours of reacting at a temperature ranging from about 4° C. to about 20° C.

24. The process of claim 21, wherein said buffered water solution is prepared with L-arginine.

25. The process of claim 21, wherein an emollient is added to said zinc oxide complex.

26. The process of claim 25, wherein said emollient added to said zinc oxide complex is glycerine.

27. The process of claim 21, further comprising heating an emulsifier to a temperature of about 60° C. to about 100° C. and then adding it to said zinc oxide complex.

28. The process of claim 21, further comprising heating said zinc oxide complex to a temperature of about 60° C. to about 100° C. and then adding an emulsifier to said heated zinc oxide complex without preheating said emulsifier.

29. The process of claim 21, further comprising adding an emulsifier to said formed zinc oxide complex, wherein said emulsifier is selected from the group consisting of cetearyl alcohol, cetearyl glucoside, sodium stearoyl glutamate, or combinations thereof.

30. The process of claim 21, further comprising adding an emulsifier to said formed zinc oxide complex, wherein said emulsifier is at least one glucoside emulsifier selected from the group consisting of cocoyl glucoside, cocoyl glucoside/cetearyl alcohol, cocoyl ethyl glucoside, disodium coco-glucoside citrate, lauryl glucoside, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or mixtures thereof.

31. The process of claim 21, further comprising adding an emulsifier to said formed zinc oxide complex, wherein said emulsifier is selected from the group consisting of butylated PVP, cetyl alcohol, sodium acrylate/sodium acryloyldimethyltaurate copolymer, diethylhexyl naphthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6-hexaricinolate, polyglyceryl-4-oleate, polyglyceryl-4-oleate/PEG-8 propylene glycol cocoate, oleamide DEA, sodium glyceryl oleate phosphate, hydrogenated vegetable glyceride phosphates, or mixtures thereof.

32. The process of claim 21, further comprising adding an emulsifier to said formed zinc oxide complex, wherein said emulsifier is selected from the group consisting of sodium stearoyl glutamate, dioctyldodecyl stearoyl glutamate, TEA-cocoyl glutamate, TEA-lauryl glutamate, TEA-stearoyl glutamate, aluminum stearoyl glutamate, monosodium glutamate, disodium glutamate, or mixtures thereof.

33. The process of claim 21, further comprising the step of adding carrot oil as an emulsifier to said formed zinc oxide complex, wherein said carrot oil imparts a darker, UV-absorbing color to said composition.

34. The process of claim 21, further comprising adjusting the degree of water-resistance of the formed zinc oxide complex by adding at least one emulsifier to said formed zinc oxide complex.

* * * * *